United States Patent [19]
Uthne et al.

[11] 3,953,290
[45] Apr. 27, 1976

[54] POLYPEPTIDES AS VITRO ACTIVE CELL GROWTH ENHANCING FACTORS AND METHODS OF USE

[75] Inventors: Knut Öivind Uthne, Sodertalje; Gustaf Bertil Åberg, Bromma, both of Sweden

[73] Assignee: AB Kabi, Stockholm, Sweden

[22] Filed: Apr. 30, 1973

[21] Appl. No.: 355,745

[52] U.S. Cl. .................................... 195/1.8; 195/1.7
[51] Int. Cl.² .......................... C12B 3/12; C12B 3/14
[58] Field of Search ............................. 195/1.7, 1.8

[56] References Cited
UNITED STATES PATENTS

| | | | |
|---|---|---|---|
| 3,122,476 | 2/1964 | Gaeta | 195/1.8 |
| 3,128,228 | 4/1964 | Michl | 195/1.8 |
| 3,429,867 | 2/1969 | Bozicevich | 195/1.8 |

OTHER PUBLICATIONS

Willmer, Cells & Tissues in Culture, Vol. 1 (1965), pp. 291–292.

*Primary Examiner*—Sam Rosen

[57] ABSTRACT

Disclosed are in vitro active cell growth factors that stimulate deoxyribonucleic acid synthesis in the cells, are polypeptide in chemical structure, having a molecular weight range of from 4,000 to 6,000 and an isoelectric range of from pH 4.3 to 5.3, are inert to about 72% aqueous ethanol containing by volume about 0.047% of concentrated hydrochloric acid, soluble in and precipitated from such acid aqueous ethanol solution by admixing in it 3.5 times its volume of a mixture of five parts of acetone with three parts of ethanol, and are soluble in about twice their weight of 20% formic acid.

12 Claims, No Drawings

POLYPEPTIDES AS VITRO ACTIVE CELL GROWTH ENHANCING FACTORS AND METHODS OF USE

This invention is that of certain polypeptides as cell growth enhancing factors (conveniently briefly called "in vitro active cell growth factors") active in vitro to stimulate animal tissue cell growth as manifested by stimulating deoxyribonucleic acid synthesis (i.e. DNA-synthesis) in animal tissue cell growth culture media.

The invention includes also the method of deriving said in vitro active cell growth factors from human, bovine or equine blood plasma or serum, or from a certain precipitate (or fraction) or certain solution derived therefrom, as more specifically described further below. Also part of the invention is the method of enhancing the in vitro cultivation of human tissue cell cultures or said cell growth in cell culture media.

The in vitro cultivation of animal tissue cells, especially of human origin, is of growing importance, for example, for the production of medically valuable biologicals such as vaccines, interferons, etc. For their growth such cells normally need sterile serum in a concentration that depends on the cell type, type of medium, and other criteria. Often bovine serum is used, and in many such cases fetal bovine serum is added to the cell culture medium.

Proteins foreign to the cell species have been used because the addition of a few percent of serum or a serum dialysate to the culture medium used for the cell cultivation enhances cell growth and also the cells grow more evenly and attach better to the surface of the vessel used.

Then also, when the desired products of these cell cultures are isolated, the foreign proteins from the medium used in the culture are very difficultly removed, or even impossible to remove, and hence may provoke immunization. This problem is accentuated when, for instance, in vaccine production human tissue cells are used and serum of animal origin is added to the cultures. That is so because, for example, in a vaccine foreign proteins might produce not only immunization but also anaphylactic shock or anaphylactoid reactions of various kinds—some potentially fatal—to the patient.

The in vitro active cell growth factors of the invention can be used then instead of serum in the cell culture medium used for growing cells in vitro; and thus overcome the aforesaid difficulties so that it no longer would be necessary to add to the medium such a heterogeneous mixture as serum.

The in vitro active cell growth factors of the invention are derived in the form of a polypeptide concentrate from the plasma or serum source starting material. Broadly considered, the invention product-wise provides in vitro active cell growth factors that are polypeptide in chemical structure, having a molecular weight range of from 4,000 to 6,000, an isoelectric range from pH 4.3 to 5.3, and stimulate animal tissue cell growth which is manifested by enhanced stimulation of DNA-synthesis in the cell growth culture medium.

Thus the cell growth stimulation provided by the polypeptide in vitro active cell growth factors of this invention may be evaluated by the extent of increase in DNA-synthesis in the cell culture medium.

The in vitro active cell growth factors of the invention are obtained from the starting material, plasma or serum of human, equine or bovine blood origin, or the Chn et al., Jour. Amer. Chem. Soc., volume 72 (1950) page 465, precipitate IV or solution IV—6 + 7, by a method having the combination of readily usable steps, which stemmed from the investigation which provided the cell growth factors of the invention.

In this investigation applicants discovered that the Cohn et al. precipitate IV, heretofore a waste product, comprised a large portion of proteins, with which there was linked or aggregated by chemical bond certain factors. Applicants in time discovered their practical combination of steps that enabled them to disaggregate and split off these factors from the carrier proteins, and later found that these factors are polypeptides and effective in vitro to enhance tissue cell growth.

This combination of steps in obtaining these polypeptide in vitro active cell growth factors involves (a) subjecting the starting material simultaneously to the action of (i) a compatible mineral acid (such as customary concentrated hydrochloric acid) to hydrolyze the bond linking, and thus split and disaggregate, these polypeptide active factors from their aggregation with their carrier proteins, and (ii) a water-miscible lower alkanol (such as 96 percent ethanol) to precipitate the proteins, (b) separating the precipitate from the hydrochloric acid and ethanol solution (e.g. by centrifugation and decanting the solution), (c) and mixing that supernatant with a polypeptide-precipitating agent (e.g. a mixture of about 5 parts of acetone and 3 parts of ethanol) at a temperature below 0° C. and about −15° C., (d) decanting the supernatant and separating the precipitate, and (e) drying the precipitate (preferably under vacuum after intermediate washing with the precipitant solution.)

The resulting dried powder is extracted with a compatible polypeptide solvent (such as 20 percent formic acid solution in distilled water), and (f) subjecting the resulting solution to gel filtration followed by elution of the desired active factors from the gel.

The in vitro active, cell growth factors of the invention are applicable to enhance the growth of any of the animal tissue cells that are cultivated in vitro, for example, human adult glia-cells, embryonic meningocytes, embryonic rat cells, lung fibroblasts, human adult skin fibroblasts, and others. For example, the cells are initially subcultivated in a minimum essential incubation medium contained in a small amount, say, 10% fetal calf serum (mixed with some antibiotics) for an initial incubation period in which the cells attach themselves to the surface of the cultivation dish; thereafter the initial incubation medium is poured off and replaced by a culture medium free of calf serum but containing a cell growth effective concentration of the polypeptide, cell growth factors of this invention.

The several aspects of the invention, namely, the derivation of its cell growth factors from starting material, these polypeptide factors themselves, and the method of enhancing in vitro cell growth by their use, are illustrated by, but not limited to, the following examples:

EXAMPLE 1

Polypeptide Cell growth factors from Cohn et al. precipitate IV: a. 30 kilograms (kg.) of Cohn et al. precipitate IV (obtained by fractionation of human plasma by their method, and corresponding to 1,000 kg. original weight of starting pooled human plasma) was homogenized with 40 liters of cooled distilled water for 120 minutes. The homogenate was admixed with three times its volume of cooled 96 percent ethanol and 0.063 of its volume of customary concentrated hydrochloric acid.

After mixing for 60 minutes at 0° C., the mixture was centrifuged (at 5,000 r.p.m. in a Sharples continuous centrifuged fed at 75 liters per hour, stopped every 15 minutes to remove and discard each time 5 kg. of precipitate containing 40% of liquid), and the supernatant was decanted and adjusted with 4 M sodium hydroxide to a pH of 8.4. The resulting precipitate was centrifuged down and the supernatant decanted and treated at −15° C. with 3.5 times its volume of a mixture of 5 parts of acetone to 3 parts of ethanol. The resulting precipitate was left to settle down during 24 hours and was collected after decanting off the supernatant, was washed twice with the same mixture of acetone and ethanol at 0° C., and then vacuum dried (without heating).

b. Extraction from the dried product: 150 grams of the foregoing vacuum dried powder product were admixed at room temperature for 60 minutes with 320 ml. of 20% formic acid (in distilled water). The mixture was then centrifuged at 5,000 r.p.m. and the supernatant extract was withdrawn. The precipitate residue was extracted likewise with 20% formic acid, and its supernatant withdrawn and pooled with the first extract and held at −20° C.

c. Further separation by gel filtration: The combined formic acid extracts were passed at 3° C. (at a rate of 350 ml. per hour) through a 10 cm. diameter by 100 cm. high column packed with the SEPHADEX G-75 beads of a three-dimensional network of dextran chains cross-linked with epichlorhydrin (product of Pharmacia Fine Chemicals, Uppsala, Sweden, and Piscatawny, N.J.). After 270 ml. of the formic acid extract had passed through the column, the SEPHADEX G-75 beads were eluted with a 1% solution of formic acid in distilled water; and the fractions corresponding to Kd-values (as defined by Bertil Gelotte, Jour. of Chromatography, volume 13, 1964, page 330) of 0.60 − 0.80 were pooled and lyophilized.

d. Characterization of the Kd-values 60 − 80 eluates: Preparative isoelectric focusing (for which see B. J. Radola, Biochim., Biophys. Acta, volume 194, 1969, page 335) was performed on the eluates from the above SEPHADEX G-75 fractionation, which above have Kd-values 0.60 − 0.80. 200 mg. of substance from each eluate were separated in a bed of SEPHADEX G-75 and 8 M aqueous urea, and the pH-gradient of the system was adjusted from pH 3 − 10 with AMPHO-LINE (polycarboxylic acids product of Aminkemi, Box 20105, Stockholm, Sweden, and sold by LKB-Produkter, Stockholm, Sweden). The bed dimensions were 0.4 × 16 × 48 cm., the current potential 10 − 15 volts per cm., and the separation time was 20 hours. From the bed 2 cm. width strips were cut and eluted with redistilled water for determination of pH and absorption at 260 nm. wave length.

These eluates from the SEPHADEX G-75 column contain a group of factors having a molecular weight range of 4,000 to 6,000 and showing DNA-synthesis stimulating activity in tissue cell cultures. Their DNA-synthesis activity was measured by the incorporation of $^3$H-thymidine (i.e. tritiated thymidine), as in the shortly below described procedure. In isoelectric focusing with the system described above, this activity was confirmed as to the factors in the pH interval of 4.3 to 5.3.

For further characterization, high voltage electrophoresis on paper was carried out at pH 2.0 using a buffer consisting of 67 ml. of formic acid, 267 ml. of acetic acid and 2666 ml. of distilled water. 1 mg. of lyophilized substance from the gel chromatography with Kd-values 0.60 to 0.80 is applied per cm. paper and separated at 10 to 12 volts per cm. for 5 hours followed by elution with 0.2 M acetic acid. The component carrying the cell growth activity migrated 0.7 − 1.2 relative to serine in this system.

EXAMPLE 2

Polypeptide Cell growth factors from horse plasma: The in vitro active cell growth factors of the invention also were obtained from plasma, by treating 1 kg. of horse plasma at 0° C. in 3 times its volume of 96 percent ethanol and 0.063 of its volume of concentrated hydrochloric acid, at 0° C. for 60 minutes. The mixture then was centrifuged at 5,000 r.p.m. and the resulting supernatant was decanted and adjusted to pH 8.4 with 4 M sodium hydroxide. The resulting precipitate was treated, extracted, dried, and separated by gel filtration all as in Example 1.

The polypeptide in vitro cell growth factors of the invention can be obtained from the Cohn et al. solution IV − 6 + 7 by following the procedure as in Example 1, and also can be obtained from human or bovine plasma or serum and also from horse serum by a procedure such as that of Example 2. To avoid unnecessarily extending the disclosure, the various procedures for obtaining the cell growth factors from these additional starting material sources are to be considered as if they appear herein written out in full.

Procedure for determining in vitro cell growth activity:

The method for determination of DNA-synthesis stimulating activity by the incorporation of $^3$H-thymidine in cells cultured in vitro is that designed by Ponten & Westermark (J. Cell Physiol., In Press) and includes the following steps:

Human glia-cells are generated from biopsy specimens taken in connection with neurosurgery. These cells are seeded out in an incubation medium (e.g. MEM) and left to form a dense monolayer (of cells), then harvested and subcultivated twice with the aid (e.g. brushing over them) of a thin film of 0.25 percent trypsin in phosphate buffered isotonic (i.e. physiological, 0.9%) saline. The cells are kept in Eagle's minimum essential medium (MEM) to which 10 percent fetal calf serum is admixed together with 100 IU of penicillin per ml. and 50 $\mu$g. of streptomycin per ml. and 1.25 $\mu$g. amphotericin B per ml. During the test the cells are grown in (universally used) FALCON dishes, and to each dish 1 to 2 × 10$^5$ cells per cm.$^2$ are added. After 24 hours the incubation medium is replaced by thymidine-free Ham F-12 (Ham, Proc. N.Y. Acad. Sci., volume 53, 1965, page 288, per Index Medicus, volume 6, 1965, page N618) without extra calf serum, but containing 15 micromoles HEPES (a non-toxic buffer substance, N-2-hydroxyethylpiperazine N-2-ethanesulfonic acid, frequently added to culture media to maintain pH, product of Sigma, St. Louis, Missouri, USA).

The serum or the eluates, the DNA-synthesis activity of which is to be determined, is added at 2 to 3 different dose levels and preincubated for 24 hours in Ham-F-12-Hepes free from calf serum. At the end of this period 2 microcuries $^3$H-thymidine is added and the incubation is continued for another 24 hours. The amount of $^3$H-thymidine incorporated is measured as $^3$H according to Westermark (Exp. Cell. Res., volume 69, 1971, page 259).

The enhancement of in vitro growth of tissue cells provoked by the inclusion of the polypeptide cell growth factors of the invention is illustrated by, but not limited to, the following examples:

EXAMPLE 3

Growth factors added to glia cells: Human glia-like cells were cultivated according to the general procedure described above (last paragraph of page 8, excluding the use of $^3$H-thymidine). To them were added 25 micrograms of the polypeptide cell growth factors according to the invention dissolved in 50 microliters of the Ham F-12 medium. After an additional cultivation period of 48 hrs., by the foregoing test stimulation of DNA-synthesis of 222 percent was observed.

EXAMPLE 4

Growth factors added to fibroblasts: Adult skin fibroblasts of human origin were cultivated and polypeptide cell growth factors added as described in Example 1. An increase in DNA-synthesis was observed reaching 294 percent stimulation.

EXAMPLE 5

Growth factors for meningocytes: Human embryonic meningocytes were cultivated and stimulated according to Example 1. Stimulation of DNA-synthesis amounted to 170 percent as compared with the incorporation of labeled thymidine in the absence of the polypeptide concentrate.

The DNA-stimulating activity results are summarized in Table 1, using the general procedure.

Table 1

| | Cell Type | Species | % stimulation in DNA-synthesis as measured by $^3$H-thymidine incorporation versus controls |
|---|---|---|---|
| (Ex.1) | Adult glia cells (HAG) | Man | 222 |
| (Ex.2) | Adult skin fibroblasts (HAS) | Man | 294 |
| | Embryonic lung fibroblasts (HEL) | Man | 116 |
| (Ex.3) | Embryonic meningocytes (HEM) | Man | 170 |
| | Embryonic lung fibroblasts (CEL) | Cat | 159 |
| | Embryonic rat cells (ERF) | Rat | 154 |

Dose-response data of the stimulatory effect on the synthesis of cell DNA is shown in Table 2.

Table 2

| Dose | | Cpm** per culture | | Ratio |
|---|---|---|---|---|
| Serum | CGF* | Serum | CGF | CGF/serum |
| | 2.5 μg. | | 1793 | |
| 0.5% | 5.0 μg. | 2388 | 2566 | 1.07 |
| | 10.0 μg. | | 2669 | |
| 1.0% | 16.6 μg. | 3148 | 3194 | 1.02 |
| 2.0% | 25.0 μg. | 3456 | 3526 | 1.02 |
| 4.0% | 50.0 μg. | 3312 | 3286 | 0.99 |

*CGF = Cell growth factors according to invention
**CPM = Counts per minute

The parallelism between increase of dose and increase in $^3$H-thymidine incorporation is noteworthy.

By using microautoradiography it was shown that the effect of the eluate was not an increased incorporation of $^3$H-thymidine (or $^3$H$^+$) but an increase of the number of cells stimulated. These results are shown in Table 3.

Table 3

| Test substance | % cells with $^3$H out of total cell number in culture |
|---|---|
| Control | 26 |
| 2% calf serum in medium | 61 |
| Cell growth factors according to invention 25 microgram per ml. | 56 |

Counts per minute expresses per culture the amount of radioactive thymidine incorporated into the DNA of the cells. The incorporation is proportional to the stimulation. CPM per culture means the total amount of activity incorporated in the whole culture (e.g. of 5 ml.).

While the invention has been explained by detailed description of certain specific embodiments of it, it is understood that various substitutions and/or modifications can be made in any of them within the scope of the appended claims which are intended to cover also equivalents of any of the specific embodiments.

What is claimed is:

1. In vitro active cell growth factors derivable from animal blood plasma or serum, or the Cohn et al. precipitate IV or solution IV—6 + 7, and characterized in that they
   i. stimulate deoxyribonucleic acid synthesis in the cells,
   ii. are polypeptide in chemical structure,
   iii. have a molecular weight range of from 4,000 to 6,000 and
   iv. an isoelectric range of from pH 4.3 to 5.3,
   v. are soluble in and otherwise inert to about 72% aqueous ethanol containing by volume about 0.047% of concentrated hydrochloric acid,
   vi. remain soluble in that aqueous ethanol after it is adjusted with 4M sodium hydroxide to pH 8.4,
   vii. are precipitated from the resulting pH 8.4 aqueous ethanol solution by admixing that ethanol solution of pH 8.4 with 3.5 times its volume of a mixture of 5 parts of acetone with 3 parts of ethanol, and
   viii. are soluble in about twice their weight of 20% formic acid.

2. Cell growth factors as claimed in claim 1, wherein said animal is a human.

3. Cell growth factors as claimed in claim 1, wherein said animal is an equine animal.

4. Cell growth factors as claimed in claim 1, wherein said animal is a bovine animal.

5. Cell growth factors as claimed in claim 1, characterized by being derived from blood plasma.

6. Cell growth factors as claimed in claim 1, characterized by being derived from Cohn et al. precipitate IV.

7. In the in vitro cultivation of tissue cell cultures, the improvement which is the step of enhancing said cultivation by adding to the culture medium a tissue cell growth enhancing effective amount of polypeptide in vitro active cell growth factors as claimed in claim 1.

8. The improvement in tissue cell cultivation as claimed in claim 7, wherein the plasma or serum is derived from human blood.

9. The improvement in tissue cell cultivation as claimed in claim 7, wherein the plasma or serum is derived from equine animal blood.

10. The improvement in tissue cell cultivation as claimed in claim 7, wherein the plasma or serum is derived from bovine animal blood.

11. The improvement in tissue cell cultivation as claimed in claim 7, wherein said growth factors are derived from plasma.

12. The improvement in tissue cell cultivation as claimed in claim 7, wherein said growth factors are derived from the Cohn et al. precipitate IV.

* * * * *

UNITED STATES PATENT AND TRADEMARK OFFICE
CERTIFICATE OF CORRECTION

PATENT NO. 3,953,290

DATED April 27, 1976

INVENTOR(S) Knut Öivind Uthne and Gustav Bertil Åberg

It is certified that error appears in the above-identified patent and that said Letters Patent are hereby corrected as shown below:

In item [54], line 1, after "AS" insert -- IN --. Column 1, line 1, after "AS" insert -- IN --. Column 2, line 2, "Chn" should read -- Cohn --. Column 3, line 7, "centrifuged" should read -- centrifuge --.

Signed and Sealed this

Sixteenth Day of November 1976

[SEAL]

Attest:

RUTH C. MASON
Attesting Officer

C. MARSHALL DANN
Commissioner of Patents and Trademarks